United States Patent [19]

Galantay et al.

[11] 3,997,664
[45] * Dec. 14, 1976

[54] SUBSTITUTED CARBINOL DERIVATIVES

[75] Inventors: Eugene E. Galantay, Morristown; Dietmar A. Habeck, Dover, both of N.J.

[73] Assignee: Sandoz, Inc., E. Hanover, N.J.

[ * ] Notice: The portion of the term of this patent subsequent to Mar. 6, 1990, has been disclaimed.

[22] Filed: Mar. 24, 1975

[21] Appl. No.: 561,487

Related U.S. Application Data

[63] Continuation of Ser. No. 114,080, Feb. 9, 1971, abandoned, which is a continuation-in-part of Ser. No. 39,546, May 21, 1970, abandoned, which is a continuation-in-part of Ser. No. 778,777, Nov. 25, 1968, abandoned.

[52] U.S. Cl. .............................. 424/238; 260/397.4; 260/397.5; 260/239.5; 260/239.55 R
[51] Int. Cl.$^2$ ................... C07J 21/00; C07J 17/00; C07J 9/00; A61K 31/56
[58] Field of Search ... 260/397.4, 239.55, 239.55 R, 260/397.5; 424/238

[56] References Cited

UNITED STATES PATENTS

| | | | |
|---|---|---|---|
| 2,930,805 | 3/1960 | Marshall | 260/397.4 |
| 3,012,045 | 12/1961 | Colton et al. | 260/397.4 |
| 3,064,014 | 11/1962 | Jongh et al. | 260/397.5 |
| 3,109,850 | 11/1963 | Wettstein et al. | 260/397.5 |
| 3,301,880 | 1/1967 | Van Vliet et al. | 260/397.5 |
| 3,318,922 | 5/1967 | Windholz et al. | 260/397.4 |
| 3,336,347 | 8/1967 | Engelfried et al. | 260/397.5 |
| 3,340,279 | 9/1967 | Jongh et al. | 260/397.4 |
| 3,392,165 | 7/1968 | Edwards et al. | 260/239.55 |
| 3,392,166 | 7/1968 | Edwards et al. | 260/239.55 |
| 3,479,376 | 11/1969 | Buzby, Jr. et al. | 260/397.45 |
| 3,507,857 | 4/1970 | Ledig | 260/239.5 |
| 3,518,255 | 6/1970 | Gardolfi et al. | 260/239.55 |

FOREIGN PATENTS OR APPLICATIONS

| | | | |
|---|---|---|---|
| 374,655 | 3/1964 | Switzerland | 260/239.55 |

*Primary Examiner* — Elbert L. Roberts
*Attorney, Agent, or Firm* — Gerald D. Sharkin; Richard E. Vila; Frederick H. Weinfeldt

[57] ABSTRACT

The compounds are steroidal 17-propadienyl carbinols and derivatives thereof. The compounds have estrogenic/progestational activity.

58 Claims, No Drawings

SUBSTITUTED CARBINOL DERIVATIVES

This is a continuation of copending application Ser. No. 114,080, filed Feb. 9, 1971 (now abandoned) which in turn is a continuation-in-part of then copending application Ser. No. 39,546, filed May 21, 1970 (now abandoned) which in turn is a continuation-in-part of then copending application Ser. No. 778,777, filed Nov. 25, 1968 (now abandoned).

This invention relates to substituted steroids. More particularly it relates to steroidal 17α-propadienyl-substituted carbinols and to the preparation thereof, as well as intermediates therefor.

The substituted carbinols of this invention may be represented by the following structural formula:

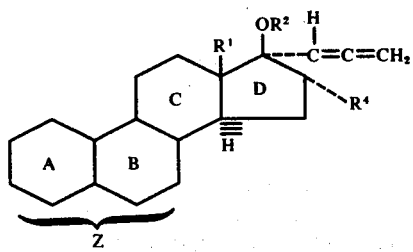

where
$R^1$ is alkyl having from 1 to 3 carbon atoms, e.g. methyl, ethyl, propyl;
$R^2$ is a hydrogen atom, methyl, acetoacetyl, or lower alkanoyl, e.g. having from 2 to 4 carbon atoms, such as, acetyl, propional or butyryl;
$R^4$ is a hydrogen atom, hydroxy, acetoacetoxy or lower alkanoyloxy, e.g. having from 2 to 4 carbon atoms; and
Z embracing rings A and B and the substituents thereon is

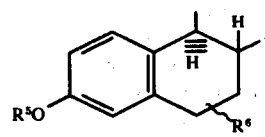 $Z1$, 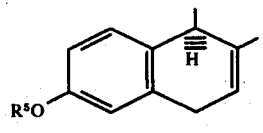 $Z2$, 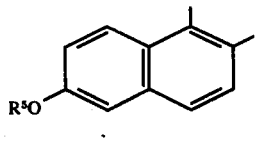 $Z3$,

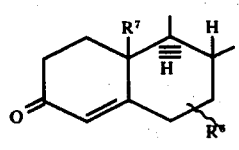 $Z4$, 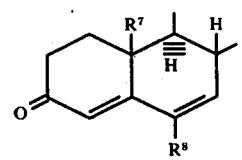 $Z5$, 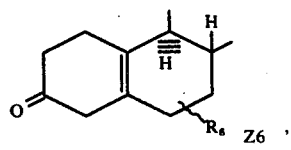 $Z6$,

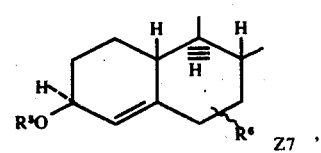 $Z7$, 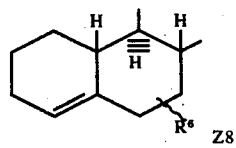 $Z8$ where
$R^5$ is a hydrogen atom, lower alkyl, e.g. having 1 to 3 carbon atoms, acetoacetyl, cycloalkyl, e.g. having from 5 to 6 carbon atoms; or lower alkanoyl, e.g. having 2 to 4 carbon atoms;
$R^6$ is a hydrogen atom, 6α-methyl or 7α-methyl;
$R^7$ is a hydrogen atom, or methyl; and
$R^8$ is a hydrogen atom, halogen having an atomic weight of about 19 to 36, i.e. fluoro or chloro, or methyl;
provided that when Z is Z1 and $R^6$ is hydrogen and any of $R^2$ and $R^5$ are either a hydrogen atom or lower alkanoyl, then $R^4$ represents a hydrogen atom.

The process for preparing the compounds of Formula (I) where $R^2$ is H, may be represented by the following reaction Scheme A:

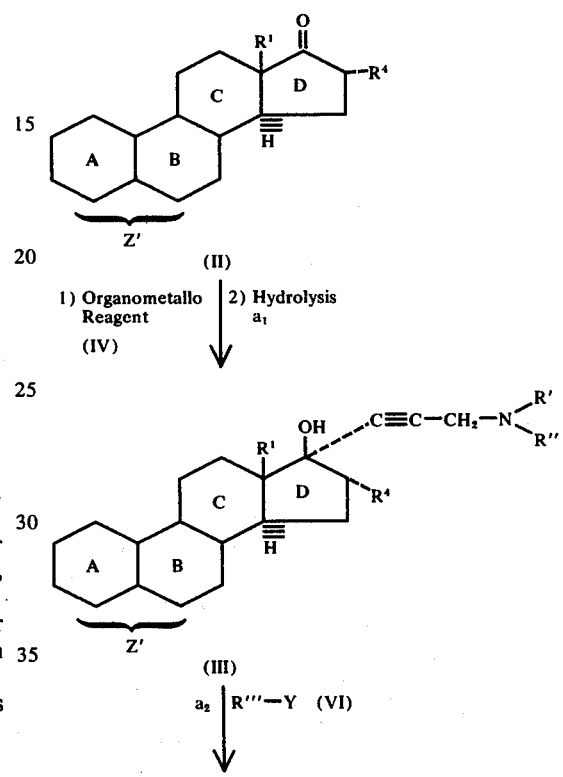

-continued

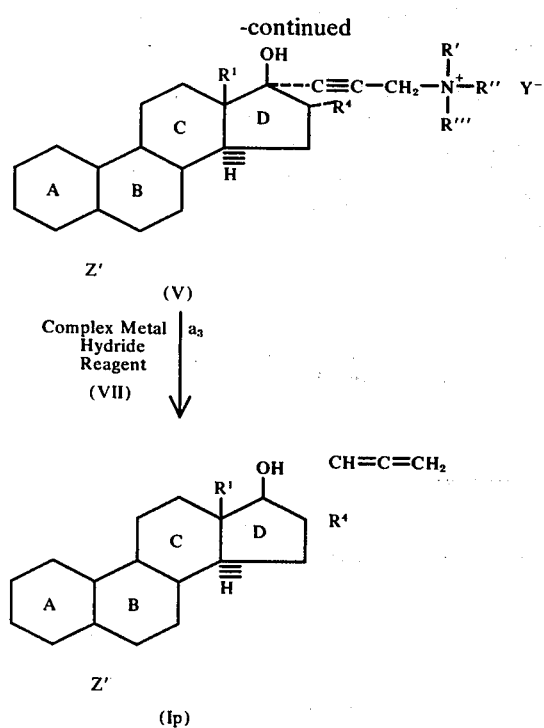

(V)

Complex Metal Hydride Reagent (VII) | $a_3$ (Ip)

wherein $R^1$ and $R^4$ have the above stated significance, each of R' and R'' is, independently, lower alkyl, e.g. having 1 to 3 carbon atoms, e.g. methyl, ethyl and propyl, or may be joined to form, together with the nitrogen atom a N-heterocyclic ring having from 4 to 6 members, e.g. a pyrrolidino or piperidino ring, and R''' is lower alkyl, e.g. having from 1 to 3 carbon atoms, Z' is either Z or if the particular group Z is affected under the reaction conditions of steps $a_1$, $a_2$ and $a_3$, it is a protected form of Z as indicated below.

Y is an anion derived from a mineral acid, e.g. a halogen atom havinng a molecular weight of from 35 to 127, i.e. chloro, bromo or iodo, or a anion derived from an organic sulfonic acid, i.e. an alkyl sulfonic acid, such as methylsulfonic acid, or aromatic sulfonic acid, such as p-toluene sulfonic acid; provided that Y is not fluoro.

The organometallo reagent (IV) has the formula

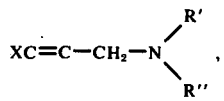

where X is Li, K, Na, Al/3, Zn/2, -MgBr, or -MgI, and R' and R'' are as defined above, and is prepared by methods disclosed in the literature. Preferably R', R'' and R''' are all methyl and Y is iodo.

With respect to Reaction Scheme A, above, Compound (III) is prepared by treating a corresponding 17-ketosteroid (II) with reagent (IV) in a solvent at a temperature of −30° to 100° C., preferably −20° C to 50° C. followed by standard hydrolysis of the resulting adduct in neutral or basic aqueous medium, e.g. water, dilute caustic or saturated ammonium chloride solution. The solvent used is dependent upon the composition of the organo-metallo reagent. For example, if X is MgBr, MgI or Li, the solvent may be ether or tetrahydrofuran, if X is Na, the solven may be liquid ammonia-ether, liquid ammonia-tetrahydrofuran, dioxane, pyridine or dioxanepyridine. Particularly advantageous is the use of lithium as X, in the presence of complexing amines, e.g. ethylenediamine. This process is represented by Step $a_1$. The temperature and solvent are not critical.

Compound (V) is prepared by treating Compound (III) with Compound (VI) in a solvent such as acetone, etc., at a temperature of −20° C to 30° C. This is represented by Step $a_2$. The temperature and solvent are not critical.

The complex metal hydride reagent (VII) used in step $a_3$ of Reaction Scheme A is a hydride ion source; such as a complex hydride of the formula VIIa:

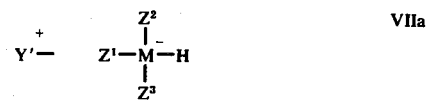

wherein
Y' is an alkali or alkaline earth metal, such as lithium, sodium, potassium, calcium or magnesium,
M is a "tervalent" transition metal or nonmetal such as aluminum, gallium or boron, i.e., an element of Group IIIa of the periodic table having atomic weight of from about 10 to 70; and each of $Z^1$, $Z^2$ and $Z^3$ is, independently, a hydrogen atom, lower alkyl, lower alkoxy or lower alkoxyalkoxy; or of the formula (VII

wherein M is as defined above and each of $Z^4$ and $Z^5$ is, independently, a hydrogen atom or lower alkyl.

The alkyl, alkoxy or alkylidene and alkyloxy moieties of the hydride ion sources (Compounds VIIa or VIIb) have from 1 to 6 carbons, and they include the isomeric forms where they exist. Representative of hydride ion sources are lithium aluminum hydride, lithium borohydride, sodium dihydrobis (2-methoxyethoxy) aluminate, lithium gallium hydride, magnesium aluminum hydride, lithium diisobutylmethyl aluminum hydride, lithium trimethoxy aluminum hydride, diethyl aluminum hydride and diborane; lithium aluminum hydride being preferred.

Step $a_3$ should be carried out in an aprotic inert medium, e.g., an ether such as diethyl ether, tetrahydrofuran or dioxane, or an aromatic medium, such as benzene or toluene or pyridine. The use of a medium which is capable of dissolving compound II, the quaternary ammonium intermediate, at the reaction temperature is preferred. The medium may be a mixture or a single material; pyridine being particularly advantageous. The reaction, e.g., may be carried out at from about −20° to +120° C, e.g., at the boiling point of the medium, however, it is preferred to employ temperatures Ip from about 0° to +40° C. While the higher temperatures result in a faster reaction rate, reactions carried out at lower temperature tend to give purer products. The reaction product (Compound Ip) may be recovered by conventional means, e.g. carefully adding a small amount of water or aqueous sodium sulfate to the reaction mixture, filtering off inorganic side products, or hydrolysis products of the hydride ion source, and then separating the Compound I$p$ from the organic phase by such means as precipitation, extraction, crystallization chromatography or liquid-liquid distribution.

As will be appreciated by those skilled in the art, it is preferred to exclude moisture from the reaction, e.g., by use of anhydrous solvents and conditions. The reaction may be advantageously carried out in an inert atmosphere, e.g., under nitrogen gas.

The disclosure below respecting protective groups pertains as well to the above described method for methylating and acylating compounds I$p$.

Certain reagents and compounds of Formulae II and VIII and protected forms thereof, are known and may be prepared by methods disclosed in the literature; and those compounds not specifically disclosed may be prepared according to analogous methods from known materials.

Conventional recovery techniques are utilized for obtaining the compounds of Formula (I), e.g. crystallization, column or layer chromatography, etc.

As will be appreciated by those skilled in the art that where alkanoyl or acetoacetyl-substituted compounds are desired, it is preferable that such groups be introduced subsequent to the above-described reaction $a_3$.

As indicated above, certain of the structures of Formula I represented by Z are affected by the reaction conditions of Schemes A and B. It is therefore a preferred embodiment of this invention to protect those Z structures which would be so affected, by means of standard protection groups which are stable to the reaction conditions. Such protected groups are readily transformed by known procedures to the desired Z forms.

The Z structures of Formula I which are affected by the reaction conditions of Schemes A and B are Z1, Z2, Z3 and Z7 where $R^5$ is not lower alkyl, Z4 where $R^7=H$, Z4 where $R^7=CH_3$, Z5 and Z6.

The compounds of Formula I where $R^2$ is alkanoyl may be obtained using standard acylation methods; accordingly, it is understood that in a Compound I in which $R^2$ and $R^5$ are H and $R^4$ is OH, the three hydroxy groups have different reactivities toward acylating agents and toward saponifying conditions. Hence, by methods well known in art, Compound I with any combination of mono, di- and trialkanoyloxy groups may be prepared. For example, a Compound I where each of $R^2$ and $R^5=H$, and $R^4=OH$ may be converted into a corresponding compound where $R^2=H$, $R^5=COCH_3$, and $R^4=OCOCH_3$ by use of acetic anhydride/pyridine or into a corresponding compound where each of $R^2$ and $R^5=COCH_3$, and $R^4=OCOCH_3$ by use of isopropenyl acetate/p-toluensulfonic acid, or with acetic anhydride in which calcium hydride had previously been dissolved.

The compounds of Formula I where $R^2$ is methyl may be obtained in a manner known per se, for instance by treating a Compond I$p$ at a temperature of about $-30°$ C to $30°$ C with $1–1.2$ equivalents of strong base (e.g. NaNH$_2$ or KNH$_2$ in liquid ammonia or LiCH$_3$ in ether) to form a 17-0-anion of Compound I$p$, and treating the latter, in the same mixture, with $1–50$ equivalents of methyl iodide.

Compounds of Formula I wherein any of $R^2$, $R^4$ or $R^5$ is acetoacetyl or acetoacetoxy are obtainable by reacting a compound of Formula I wherein any of proteins 3, 16$\alpha$ or 17$\beta$ is hydroxy, with a suitable reagent, e.g. diketene, under conventional conditions employed in carrying out such a reaction. For example, a hydroxy bearing compound of Formula I may be reacted with diketene in an inert organic solvent, e.g. benzene or toluene or mixture thereof, in the presence of a small amount of organic tertiary amine base, e.g. pyridine, at relatively low temperatures, e.g. at from about $-5°$ to $+35°$ C.

In accordance with an additional aspect of this invention, the compounds of Formula III, where $R^2$ is a hydrogen atom and are as defined above, may be prepared by the following reaction Scheme B. Compounds III may then be converted to Compounds I$p$ as described in Reaction Scheme A by Steps $a_2$ an $a_3$. It is appreciated that this method represented by Scheme B is particularly advantageous for the preparation of Compounds III in which the nature of the Z' ring system is such that it is not affected under the conditions of Steps $b_1$, $a_2$ and $a_3$ (e.g. Z1, Z2, Z3, Z7, Z8).

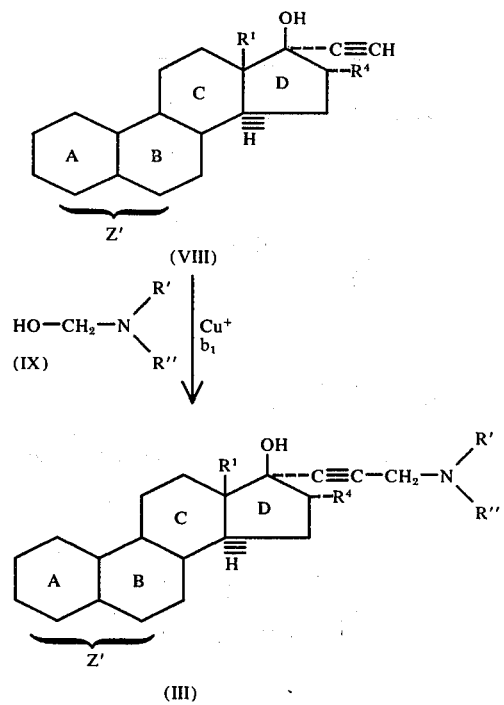

wherein $R^1$, $R^4$, $R'$, $R''$ and $Z'$ have the above-stated significance.

In this scheme, step $b_1$ is a Mannich-type reaction involving the ethynyl group in VIII; it can be carried out under conditions known to be operative in Mannich reactions of this type. Preferably, however, step $b_1$ is carried out with geminal amino alcohols of the type

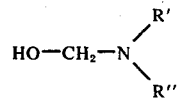

in the presence of Cu + ions and small amounts of weak acid, (e.g. acetic acid), at temperatures of $10° – 80°$ C., preferably from about $50° – 70°$ C. in inert solvents such as dioxane and tetrahydrofuran.

When the desired Z structure is Z1, Z2, Z3 or Z7 where $R^5$ is not lower alkyl, then the substituent $R^5$ is a base-stable, acid hydrolyzable protective group (P₁), e.g. tetrahydropyran-2-yl or tetrahydrofuran-2-yl.

When the desired Z structure is Z4 where R⁷ = H, then the group as protected is represented by (P₂, P₃ or P₃ₐ).

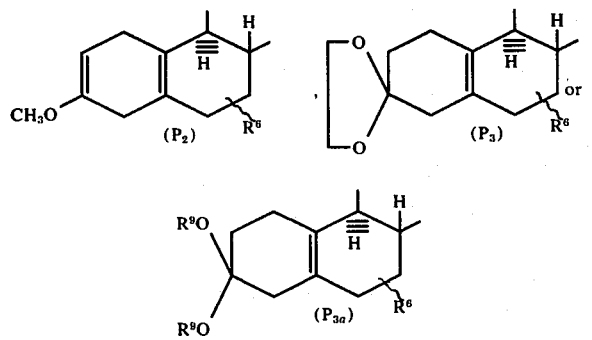

wherein R⁶ is as defined above, and R⁹ is alkyl having from 1 to 4 carbons and is linear.

When the desired Z structure is Z4, where R⁷ = CH₃, then the group as protected is represented by (P₄)

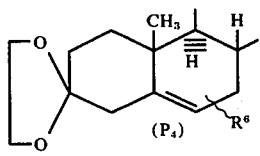

wherein R⁶ is as defined above.

When the desired Z structure is Z5 where R⁷ = H, then the group as protected is represented by (P₅ₐ), (P₅ᵦ) or (P₅c)

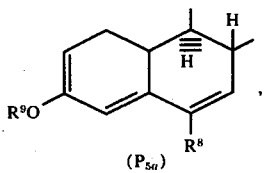

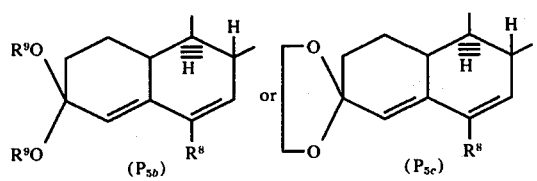

wherein R⁸ and R⁹ are as defined above.

When the desired Z structures is Z5, where R7 is methyl, then the group as protected is represented by (P₅)

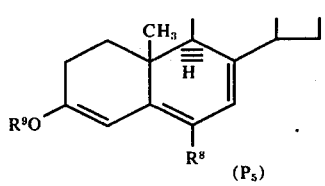

wherein R⁸ and R⁹ are as defined above.

When the desired Z structure is Z6, then the group as protected is represented by (P₂) or (P₃).

The substituted carbinol derivatives represented by Formula (I) above are useful because they possess pharmacological properties in animals. In particular, such compounds are useful as fertility control agents in animals.

Compounds (I) where Z is Z1 to Z3 possess estrogenic activity in the mouse and rat as determined by the method basically described in Endocrinology 65 (1959) 265 and Am. J. Physiol. 189 (1957) 355, respectively, and are particularly useful in treating estrogen deficiencies in animals, in controlling fertility in mammals, and in regulating estrus and the menstrual cycle. The compounds of Formula (I) wherein Z is Z4 to Z8 possess progestational activity as indicated by the well-known Clauberg test, i.e. the method basically described in Endocrinology 63 (1958) 464 wherein the rabbit is given 0.01 to 1.0 milligrams of active agent, and are particularly useful in controlling fertility in mammals and in the regulation of estrus and the menstrual cycle.

These compounds may be combined with a pharmaceutically acceptable carrier or adjuvant. They may be administered orally or parenterally. The dosage will vary depending upon the mode of administration utilized and the particular compound employed. However, in general, satisfactory results are obtained when the compounds are administered at a daily dosage of from about 0.01 milligram to 10 milligrams, particularly from about 0.05 milligram to 10 milligrams. This daily dosage is preferably given in equally divided doses, e.g. 1 to 2 times a day, or in sustained release form. It will be appreciated by those skilled in the art, that the daily dosage level is independent of body weight. Dosage forms suitable for internal administration comprise from about 0.005 milligrams to about 10 milligrams of the compound in admixture with a solid or liquid pharmaceutical carrier or diluent.

A representative formulation suitable for oral administration is a tablet prepared by standard tabletting techniques which contains the following:

| Ingredients | Parts By Weight |
|---|---|
| 17α-Propadienyl-3-methoxyestra-1,3,5,(10)-trien-17β-ol | 2.5 |
| Tragacanth | 2 |
| Lactose | 87 |
| Corn starch | 5 |
| Talcum | 3 |
| Magnesium Stearate | 0.5 |

This invention is illustrated but not limited by the following examples wherein the temperatures are centigrade:

EXAMPLE 1

17α-Propadienyl-3-methoxyestra-1,3,5(10)-trien-17β-ol

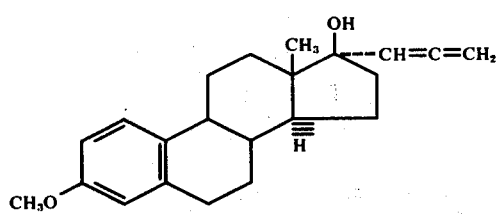

STEP 1

17α-Dimethylaminopropynyl-3-methoxyestra-1,3,5(10)-trien-17β-ol.

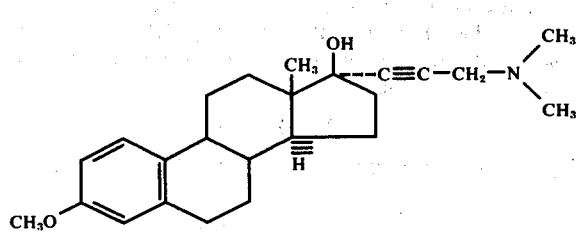

A mixture of 15.8 g of 17α-ethynyl-3-methoxyestra-1,3, 5(10)-trien-17β-ol, 15.0 ml of dimethylaminomethanol, 500 mg of cuprous chloride, 8.5 ml of glacial acetic acid and 125 ml of dioxane is kept at 70° for 5 hours. Then, ice water is added, the pH is adjusted to 10, and the product of this Step (1) extracted with ether. It remains a foam [α] $_D^{20}$ = −8.84 (C = 1, CHCl$_3$).

STEP 2

17α-Dimethylaminopropynyl-3-methoxyestra-1,3,5(10)-trien-17β-ol Methiodide.

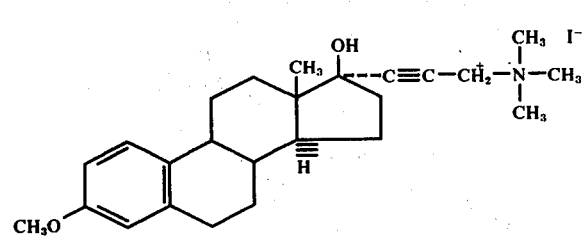

A mixture of 10.0 g. of the dimethylamino product of Step 1, 290 ml of acetone and 87 ml of methyl iodide is kept at 0° for 24 hours. The product of this Step (2) separated in crystalline form and is isolated by filtration; m.p. 237°–9°.

STEP 3

17α-Propadienyl-3-methoxyestra-1,3,5(10)-trien-17β-ol.

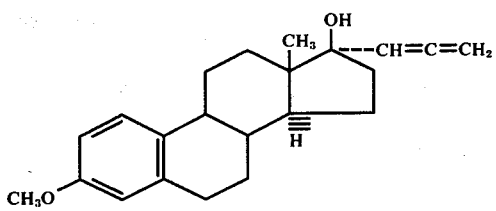

To a suspension of 3.006 g of the quaternary salt as prepared under Step 2, in 65 ml of anhydrous tetrahydrofuran, there is added, at −75°, 11.25 ml of a 0.525 molar lithiumaluminum hydride-tetrahydrofuran solution. The mixture is stirred 2 hours at −10°, during which time a clear solution is obtained; finally, it is kept at room temperature overnight. After re-cooling to 0°, saturated aqueous ammonium chloride solution is added and the title product extracted with ether. A quantitative yield overall, Steps 1, 2 and 3) of crystalline material, m.p. 129.5°– 130.5° [α]$_D$ = +7.18° (c=1, CHCl$_3$) is obtained.

EXAMPLE 2

By using the conditions described in Example 1, Steps 1, 2 and 3, respectively and in place of 17α-ethynyl-3-methoxyestra-1,3,5(10)-trien-17β-ol starting with:

a. 17α-ethynyl-3-methoxyestra-1,3,5(10), 7-tetraen-17β-ol
b. 17α-ethynyl-3-methoxyestra-1,3,5(10),6,8-pentaen-17β-ol
c. 17α-ethynylestra-4-ene-17β-ol
d. 3-Cyclopentyloxy-17α-ethynylestra-1,3,5(10)-trien-17β-ol
e. 3-Ethoxy-17α-ethynyl-13-ethylgona-1,3,5(10)-trien-17β-ol
f. 17α-ethynyl-3-methoxy-7α-methylestra-1,3,5(10)-trien-17β-ol
g. 17α-ethynyl-16α-hydroxy-3-methoxyestra-1,3,5(10)-trien-17β-ol
h. 17α-ethynylestra-4-ene-3β,17β-diol the following products are obtained:
a. 17α-propadienyl-3-methoxyestra-1,3,5(10),7-tetraen-17β-ol
b. 17α-propadienyl-3-methoxyestra-1,3,5(10),6,8-pentaen-17β-ol
c. 17α-propadienylestra-4-en-17β-ol
d. 3-Cyclopentyloxy-17α-propadienylestra-1,3,5(10)-trien-17β-ol
e. 3-ethoxy-17α-propadienyl-13-ethylgona-1,3,5(10)-trien-17β-ol
f. 17α-propadienyl-3-methoxy-7α-methylestra-1,3,5(10)-trien-17β-ol
g. 17α-propadienyl-16α-hydroxy-3-methoxyestra-1,3,5(10)-trien-17β-ol
h. 17α-propadienylestra-4-ene-3β, 17β-diol

EXAMPLE 3

17α-Propadienyl-3-methoxyestra-2,5(10)-dien-17β-ol

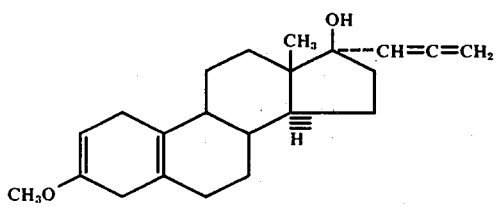

STEP 1.

17α-Dimethylaminopropynyl-3-methoxyestra-2,5(10)-dien-17β-ol.

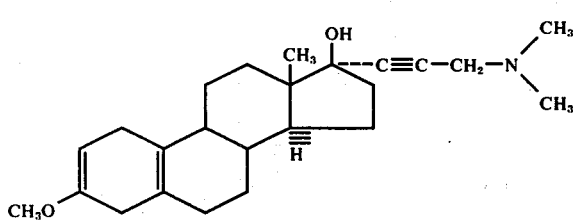

To a Grignard mixture, prepared from 1.50 g of magnesium, 4.68 g of ethyl bromide and 70 ml of tetrahydrofuran, there is dropwise added 5.3 g of dimethylaminopropyne, dissolved in 10 ml of tetrahydrofuran. After the evolution of ethane ceases, a solution of 1.716 g of 3-methoxyestra-2,5(10)-diene-17-one in 30 ml of tetrahydrofuran is dropwise added, the temperature being 0°–5° C. during addition and 20°–25° for 4 further hours. Aqueous 2 N NaOH solution (100 ml) is added and the mixture concentrated in vacuo at temperatures not exceeding 30° C. unitl the total volume is 100 ml. The concentrated mixture is then extracted with ether (5 × 25 ml), using a centrifuge to facilitate separation from the salt-containing aqueous phase. The product of this Step (1) ($a_1$) is obtained by evaporating the dried ethereal solutions and pumping off any excess dimethylaminopropyne present.

STEP 2.

17α-Dimethylaminopropynyl-3-methoxyestra-2,5(10)-dien-17β-ol Methiodide

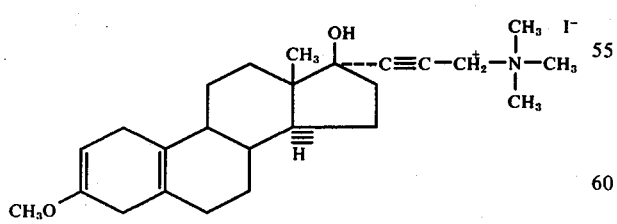

The product of Step 1 (2.0 g) is dissolved in 30 ml of acetone. After addition of 3.5 g of methyl iodide, the mixture is kept at 8° for 18 hours. The title product of this Step (2) crystallizes and is isolated by filtration and washing with anhydrous ether.

STEP 3.

17α-Propadienyl-3-methoxyestra-2,5(10)-dien-17β-ol

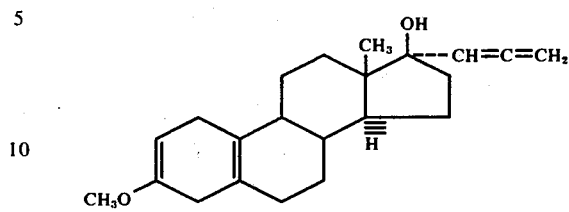

To a suspension of 2.500 g of the methiodide of Step 2, in 50 ml of tetrahydrofuran, there is added, at −75°, 9.3 ml of a 0.525 molar lithium aluminum hydride-tetrahydrofuran solution. The mixture is brought to −10° where it is stirred until (90 minutes) a clear solution is obtained. Finally, it is kept at room temperature for 12 hours. 100 ml of 2 N aqueous NaOH solution containing 50 mg di-tert.-butylcresol is added and the mixture concentrated in vacuo until the total volume is 100 ml. Extraction with 5 × 20 ml ether on the centrifuge, drying the ethereal solutions over $K_2CO_3$ and evaporation gives the title product, 17α-propadienyl-3-methoxyestra-2,5(10)-dien-17β-ol.

EXAMPLE 4

17α-Propadienylestra-5(10)-en-17β-ol-3-one

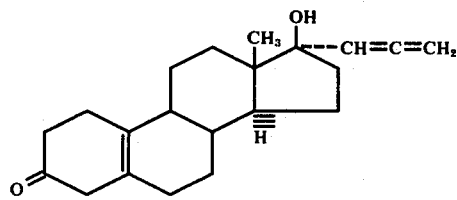

The product of Example 3, 17α-propadienyl-3-methoxyestra-2,5(10)-dien-17β-ol (2.0 g) is dissolved in a mixture of 20 ml of glacial acetic acid and 2 ml of water. After 2 hours, 200 ml of water is added and the product extracted with ethyl acetate (5 × 10 ml). Evaporation of the ethyl acetate extracts gives the title product 17α-propadienylestra-5(10)-en-17β-ol-3-one as a crystalline solid.

EXAMPLE 5

17α-Propadienylestra-4-en-17β-ol-3-one

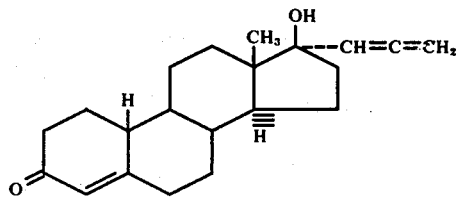

The product of Example 3, 17α-propadienyl-3-methoxyestra-2,5(10)-dien-17β-ol (5.5 g) is dissolved in a mixture of 50 ml of methanol and 1.5 ml of 11 N aqueous hydrochloric acid and is kept at 30° C. for 30 minutes. After dilution with 100 ml of water, the product is extracted with methylene chloride (5 × 15 ml). Evaporation of the dried methylene chloride solutions, followed by recrystallization of the residue from methanol yields the pure compound, 17α-propadienylestra-4-en-17β-ol-3-one.

EXAMPLE 6

By using conditions of Example 3, steps 1, 2 and 3, and Example 5, respectively and in place of 3-methoxyestra-2,5(10)-diene-17--one starting with:
a. Estrone 3-tetrahydropyranyl ether
b. 3-Methoxy-7α-methylestra-2,5(10)-dien-17-one
c. 3-Ethylenedioxy-6α-methylandrost-5-en-17-one
d. 3,3-dimethoxyestra-5(10)-en-17-one
e. 3-Ethylenedioxy-6-fluoroandrosta-4,6-diene-17-one
f. 3-Ethylenedioxy-6-chlorandrosta-4,6-diene-17-one
g. 3-Ethylenedioxy-6-methylandrosta-4,6-diene-17-one
h. 3-Methoxy-13-ethylgona-2,5(10)-dien-17-one
i. 13-n-Propyl-3β-tetrahydropyranyloxygona-2,5(10)-dien-17-one
the following products are obtained:
a. 17β-Propadienylestra-1,3,5(10)-trien-3,17β-diol
b. 7α-Methyl 17α-Propadienylestra-4-en-17β-ol-3-one
c. 6α-Methyl-17α-propadienyl androst-4-en-17β-ol-3-one
d. 17α-Propadienylestra-4-en-17β-ol-3-one
e. 6-Fluoro-17α-propadienylandrosta-4,6-dien-17β-ol-3-one
f. 6-Chloro-17α-propadienylandrosta-4,6-dien-17β-ol-3-one
g. 6-Methyl-17α-propadienylandrosta-4,6-dien-17β-ol-3-one
h. 13-Ethyl-17α-propadienylgona-4-en-17β-ol-3-one
i. 17α-propadienyl-13-n-propylgona-4-en-17β-ol-3-one

EXAMPLE 7

By using conditions of Example 3, steps 1, 2, 3 and Example 4, respectively, and in place of 3-methoxyestra-2,5(10)-diene-17-one starting with:
a. 3-Methoxy-7α-methylestra-2,5(10)-dien-17-one
b. 3-Methoxy-13-ethylgona-2,5(10)-dien-17-one
the following products are obtained:
a. 7α-Methyl-17α-Propadienylestra-5(10)-en-17β-ol-3-one
b. 13-Ethyl-17α-propadienylgona-5(10)-en-17β-ol-3-one

EXAMPLE 8

17β-Acetoxy-3-methoxy-17α-propadienylestra-1,3,5(10)-triene

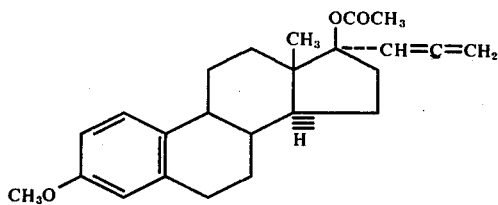

A solution of 297.8 mg of 17α-propadienyl-3-methoxyestra-1,3,5(10)-trien-17β-ol (Example 1, step 3) and 12 mg of p-toluenesulfonic acid in 6 ml of isopropenyl acetate is kept at room temperature for 18 hours. Ether is added and the solution, after washing with ice cold NaHCO₃ solution and drying over MgSO₄, is evaporated to dryness to yield, after crystallization from methanol, the title product 17β-acetoxy-3-methoxy-17α-propadienylestra-1,3,5(10)-triene, m.p. 89°–90° C., $[\alpha]_D = +9.27°$ (c=1, CHCl₃).

EXAMPLE 9

By using the conditions of Example 8, and in place of 3-methoxy-17α-propadienyl-estra-1,3,5(10)-triene-17β-ol, and starting with:
a. 17α-Propadienylestra-1,3,5(10)-trien-3,17β-diol
b. 13-n-propyl-17α-propadienylgona-4-ene-3β,17β-diol
the following products are obtained:
a. 3,17β-Diacetoxy-17α-propadienylestra-1,3,5(10)-triene
b. 3β,17β-Diacetoxy-17α-propadienyl-13-n-propyl-gona-4-ene

EXAMPLE 10

3,17β-Dimethoxy-17α-propadienylestra-1,3,5(10)-triene

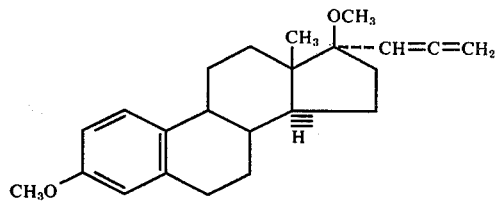

To a solution of lithium amide in liquid ammonia (prepared from 73.5 mg Li and 26 ml of NH₃) there is added a solution of 3.24 g of 17α-propadienyl-3-methoxy-estra-1,3,5(10)-trien-17β-ol (Example 1) in 50 ml of ether. After 2 hours at refluxing ammonia temperature, 2.5 g of methyl iodide is added and the ammonia allowed to escape. Addition of 50 ml of water and separation of the ether phase (and ether washup) followed by the evaporation of the dried ethereal solution yields the title compound, 3,17β-dimethoxy-17α-propadienylestra-1,3,5(10)-triene.

EXAMPLE 11

Utilizing the conditions as described in Examples 10 and 5, respectively, and in place of the 17α-propadienyl-3-methoxyestra-1,3,5(10)-trien-17β-ol used therein, starting with: )-trien-17β
a. 3-methoxy-17α-propadienylestra-2,5(10)-dien-17β-ol
b. 13-ethyl-3-methoxy-17α-propadienylgona-2,5(10)-dien-17β-ol
c. 3-methoxy-7α-methyl-17α-propadienylestra-2,5(10)-dien-17β-ol
the following products are obtained:
a. 17β-methoxy-17α-propadienylestra-4-en-3-one
b. 13-ethyl-17β-methoxy-17α-propadienylgona-4-en-3-one
c. 17β-methoxy-7α-methyl-17α-propadienylestra-4-en-3-one

EXAMPLE 12

3β,17β-Diacetoxy-17α-propadienylestra-4-ene

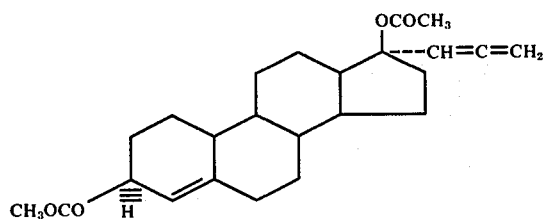

By using the conditions of Example 8 but starting with 17α-propadienylestra-4-ene-3β17β-diol, the title product, 3β,17β-Diacetoxy-17α-propadienylestra-4-ene is obtained.

EXAMPLE 13

3β-Acetoxy-17α-propadienylestra-4-en-17β-ol 0.8 g of 17α-propadienylestra-4-ene-3β,17β-diol (product of Example 2h) is added to a solution of 4.4 ml of acetic anhydride in 13.0 ml of pyridine and the resulting mixture stirred at room temperature (20°) for 17 hours, after which period the mixture is poured into 100 ml of water and extracted 5 times with 10 ml portions of methylene chloride. The combined methylene chloride extracts are dried over anhydrous sodium sulfate and the solvent removed by evaporation under vacuum to obtain a residue, which upon recrystallization from 95% ethanol yields the title product; m.p. 107° to 108.5°.

EXAMPLE 14

17β-acetoacetoxy-17α-propadienylestra-4-en-3-one

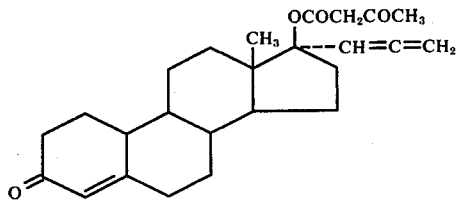

To a solution of 1.0 g of 17α-propadienylestra-4-en-17β-ol-3-one in a mixture of 18.5 ml of benzene, 9.25 ml of toluene and 0.23 ml of pyridine, there is dropwise added, at 0°, 1.8 ml of di-ketone, dissolved in 9 ml of benzene. The mixture is then kept at 25° for 3 hours. The product is isolated by washing the mixture with ice-cold 0.1 N sodium hydroxide and water, drying over anhydrous sodium sulfate, evaporating to dryness to obtain the title product.

EXAMPLE 15

3β-Acetoxy-17β-acetoacetoxy-17α-propadienyl-4-estrene may be similarly prepared, (analogously to Example 14) from 3β-acetoxy-17α-propadienylestra-4-en-17β-ol; mp 110° − 112° (from methanol).

EXAMPLE 16

17β-acetoxy-17α-propadienylestra-4-en-3-one

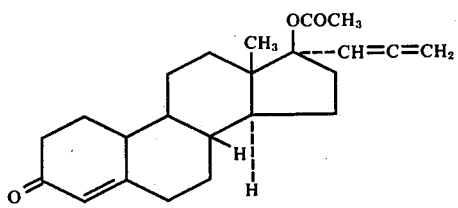

A mixture of 0.050 g of calcium hydride in 5 ml of acetic anhydride is refluxed for 1 hour then 0.5 g of 17α-propadienylestra-4-en-17β-ol-3-one is added and refluxing continued for 3 more hours. After cooling, the mixture is poured on ice and extracted with methylene chloride. The methylene chloride solution is washed with aqueous saturated sodium bicarbonate and then water, dried over anhydrous sodium sulfate and evaporated to give the title product.

EXAMPLE 17

17α-propadienyl-3-methoxyestra-1,3,5(10)-trien-17β-ol

Following the procedure described in Step 3 of Example 1, but replacing the tetrahydrofuran used therein as the suspending medium for the quaternary salt, with an equal volume of anhydrous pyridine, the title compound is obtained.

What is claimed is:

1. A compound of the formula

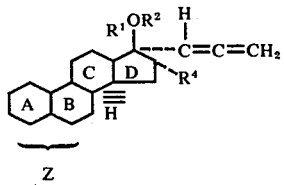

where
$R^1$ is alkyl having 1 to 3 carbon atoms,
$R^2$ is a hydrogen atom, methyl, acetoacetyl, or lower alkanoyl;
$R^4$ is a hydrogen atom, hydroxy, acetoacetoxy, or lower alkanoyloxy, and
Z embracing rings A and B and the substituents thereon is

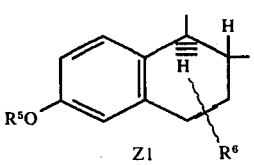 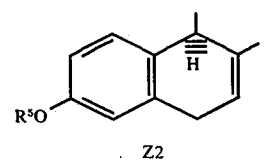

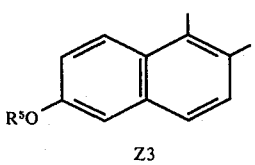 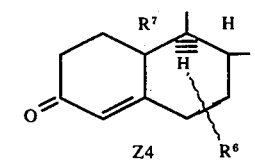

-continued

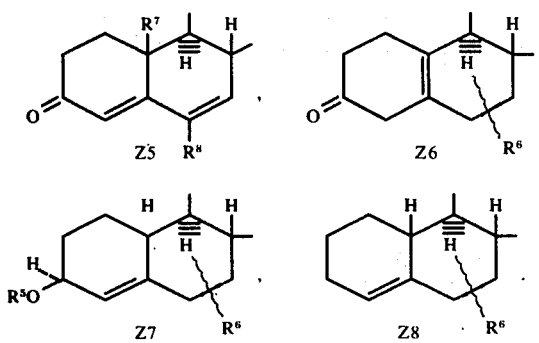

where
R⁵ is a hydrogen atom, alkyl having 1 to 3 carbon atoms, cycloalkyl having from 5 to 6 carbon atoms, acetoacetyl, alkanoyl having 2 to 4 carbon atoms;
R⁶ is a hydrogen atom, 6α-methyl or 7α-methyl;
R⁷ is a hydrogen atom, or methyl; and
R⁸ is a hydrogen atom, halogen having an atomic weight of about 19 to 36 or methyl;
provided that when Z is Z1, and R⁶ is hydrogen and any of R² and R⁵ are either a hydrogen atom or lower alkanoyl, then R⁴ represents a hydrogen atom.

2. The compound of claim 1 which is 17α-propadienyl-3-methoxy-estra-1,3,5(10)-trien-17β-ol.
3. The compound of claim 1 which is 17α-propadienyl-3-methoxy-estra-1,3,5(10),7-tetraen-17β-ol.
4. The compound of claim 1 which is 17α-propadienyl-3-methoxy-estra-1,3,5(10),6,8-pentaen-17β-ol.
5. The compound of claim 1 which is 17α-propadienylestra-4-en-17β-ol.
6. The compound of claim 1 which is 3-cyclopentyloxy-17α-propadienylestra-1,3,5(10)-trien-17β-ol.
7. The compound of claim 1 which is 3-ethoxy-17α-propadienyl-13-ethylgona-1,3,5(10)-trien-17β-ol.
8. The compound of claim 1 which is 17α-propadienyl-3-methoxy-7α-methylestra-1,3,5(10)-trien-17β-ol.
9. The compound of claim 1 which is 17α-propadienyl-16α-hydroxy-3-methoxestra-1,3,5(10)-trien-17β-ol.
10. The compound of claim 1 which is 17α-propadienylestra-4-ene-3,17β-diol.
11. The compound of claim 1 which is 17α-propadienylestra-5(10)-en-17β-ol-3-one.
12. The compound of claim 1 which is 17α-propadienylestra-4-en-17β-ol-3-one.
13. The compound of claim 1 which is 17α-propadienylestra-1,3,5(10)-trien-3,17β-diol.
14. The compound of claim 1 which is 7α-methyl-17α-propadienylestra-4-en-17β-ol-3-one.
15. The compound of claim 1 which is 6α-methyl-17α-propadienylandrost-4-en-17β-ol-3-one.
16. The compound of claim 1 which is 3β,17β-diacetoxy-17α-propadienylestra-4-ene.
17. The compound of claim 1 which is 6-fluoro-17α-propadienylandrosta-4,6-dien-17β-ol-3-one.
18. The compound of claim 1 which is 6-chloro-17α-propadienylandrosta-4,6-dien-17β-ol-3-one.
19. The compound of claim 1 which is 6-methyl-17α-propadienylandrosta-4,6-dien-17β-ol-3-one.
20. The compound of claim 1 which is 13-ethyl-17α-propadienylgona-4-en-17β-ol-3-one.
21. The compound of claim 1 which is 17α-propadienyl-13-n-propylgona-17β-ol-4-ene.
22. The compound of claim 1 which is 17β-acetoxy-3-methoxy-17α-propadienylestra-1,3,5(10)-triene.
23. The compound of claim 1 which is 3,17β-diacetoxy-17α-propadienylester-1,3,5(10)-triene.
24. The compound of claim 1 which is 3β,17β-diacetoxy-17α-propadienyl-13-n-propylgona-4-ene.
25. The compound of claim 1 which is 3,17β-dimethoxy-17α-propadienylestra-1,3,5(10)-triene.
26. The compound of claim 1 which is 17β-methoxy-17α-propadienyl-estra-4-en-3-one.
27. The compound of claim 1 which is 13-ethyl-17β-methoxy-17α-propadienylestra-4-en-3-one.
28. The compound of claim 1 which is 17β-methoxy-7α-methyl-17α-propadienylestra-4-en-3-one.
29. The compound of claim 1 which is 3β-acetoxy-17α-propadienylestra-4-en-17β-ol.
30. The compound of claim 1 which is 17β-acetoacetoxy-17α-propadienylestra-4-en-3-one.
31. The compound of claim 1 which is 3β-acetoxy-17β-acetoacetoxy-17α-propadienyl-4-estrene.
32. The compound of claim 1 which is 17β-acetoxy-17α-propadienylestra-4-en-3-one.
33. A method of controlling fertility in an animal comprising adminstering thereto an effective amount of a compound of claim 1.
34. A pharmaceutical composition comprising a compound of claim 1 and a pharmaceutically acceptable carrier therefor.
35. A compound of the formula

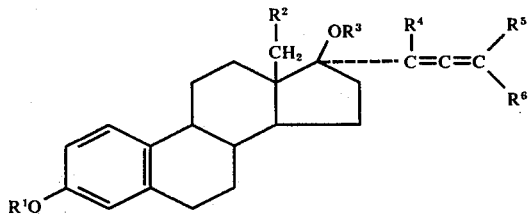

wherein:
R¹ is selected from the group consisting of hydrogen, lower alkyl having from 1 to 3 carbon atoms, cycloalkyl, lower alkanoyl of 2 to 4 carbon atoms, acetoacetyl, tetrahydropyran-2-yl and tetrahydrofuran-2-yl;
R² is selected from the group consisting of hydrogen and lower alkyl containing from 1 to 2 carbon atoms;
R³ is selected from the group consisting of hydrogen, lower alkanoyl of 2 to 4 carbon atoms and acetoacetyl; and each of R⁴, R⁵ and R⁶ is hydrogen.
36. A compound according to claim 35 wherein R¹ is methyl and R⁴, R⁵ and R⁶ are each hydrogen.
37. A compound according to claim 35 wherein R¹ is methyl and R³, R⁴, R⁵ and R⁶ are each hydrogen.
38. A compound according to claim 35 wherein R¹ is cyclopentyl and R⁴, R⁵ and R⁶ are each hydrogen.
39. A compound according to claim 35 wherein R¹ is tetrahydropyran-2-yl and R⁴, R⁵ and R⁶ are each hydrogen.
40. A compound according to claim 35 wherein R¹ is tetrahydropyran-2-yl and R³, R⁴, R⁵ and R⁶ are each hydrogen.

41. A compound according to claim 35 wherein $R^1$ is tetrahydropyran-2-yl, $R^3$ is acetyl and $R^4$, $R^5$ and $R^6$ are each hydrogen.

42. A compound according to claim 35 wherein $R^2$, $R^4$, $R^5$ and $R^6$ are each hydrogen.

43. A compound according to claim 35 wherein $R^2$ is methyl and $R^4$, $R^5$ and $R^6$ are each hydrogen.

44. A compound of the formula

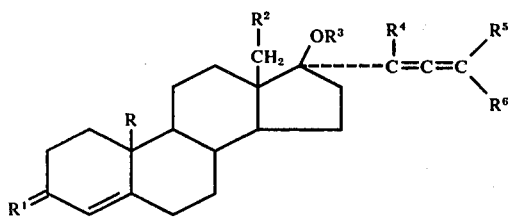

wherein $R^1$ is selected from the group consisting of oxo and the group

wherein $R^7$ is selected from the group consisting of hydrogen, hydroxy, tetrahydropyran-2-yloxy, tetrahydrofuran-2-yloxy, alkanoyloxy containing 2 to 4 carbon atoms and acetoacetyloxy;

R is selected from the group consisting of hydrogen and methyl but is hydrogen when $R^1$ is other than oxo;

$R^2$ is selected from the group consisting of hydrogen and a lower alkyl containing from 1 to 2 carbon atoms;

$R^3$ is selected from the group consisting of hydrogen, lower alkanoyl containing 2 to 4 carbon atoms and acetoacetyl;

and each of $R^4$, $R^5$ and $R^6$ is hydrogen.

45. A compound according to claim 44 wherein $R^1$ is oxo and $R^4$, $R^5$ and $R^6$ are each hydrogen.

46. A compound to claim 44 wherein $R^1$ is oxo and R, $R^4$, $R^5$ and $R^6$ are each hydrogen.

47. A compound according to claim 44 wherein R, $R^3$, $R^4$, $R^5$ and $R^6$ are each hydrogen, and $R^1$ is the group

wherein $R^7$ is hydrogen.

48. A compound according to claim 44 wherein $R^1$ is oxo and R, $R^3$, $R^4$, $R^5$ and $R^6$ are each hydrogen.

49. A compound according to claim 44 wherein R, $R^2$, $R^4$, $R^5$ and $R^6$ are each hydrogen and $R^1$ is the group

wherein $R^7$ is tetrahydropyran-2-yloxy.

50. A compound according to claim 44 wherein R, $R^2$, $R^4$, $R^5$ and $R^6$ are each hydrogen and $R^1$ is the group

wherein $R^7$ is hydroxy.

51. A compound of the formula

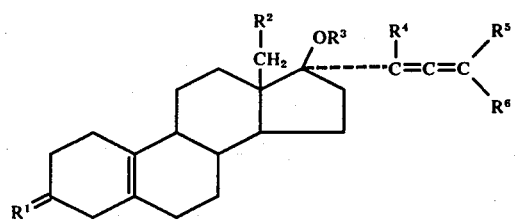

wherein $R^1$ is oxo;

$R^2$ is selected from the group consisting of hydrogen and a lower alkyl containing from 1 to 2 carbon atoms;

$R^3$ is selected from the group consisting of hydrogen, and lower alkanoyl containing 2 to 4 carbon atoms and acetoacetyl;

and each of $R^4$, $R^5$ and $R^6$ is hydrogen.

52. A compound according to claim 51 wherein $R^1$ is oxo and $R^4$, $R^5$ and $R^6$ are each hydrogen.

53. A compound according to claim 52 wherein $R^2$ is hydrogen.

54. A compound according to claim 52 wherein $R^2$ is methyl.

55. A compound according to claim 51 wherein $R^1$ is oxo and $R^3$, $R^4$, $R^5$ and $R^6$ are each hydrogen.

56. A compound according to claim 51 wherein $R^1$ is oxo, $R^3$ is acetyl and $R^4$, $R^5$ and $R^6$ are each hydrogen.

57. A steroidal compound of the formula:

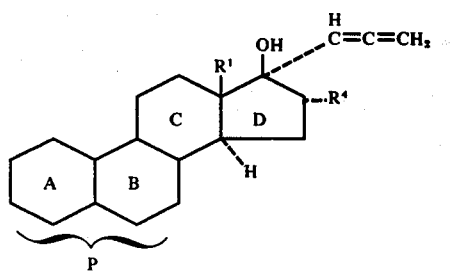

wherein $R^1$ is alkyl having from 1 to 3 carbon atoms;

$R^4$ is a hydrogen atom, hydroxy, acetoacetoxy, or lower alkanoyl having from 2 to 4 carbon atoms; and P embracing rings A and B is

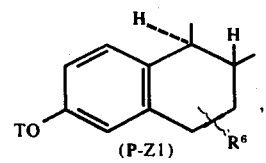
(P-Z1)
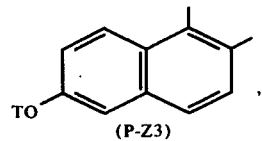
(P-Z3)
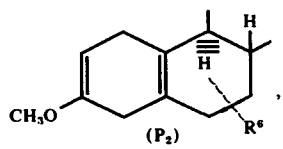
(P₂)
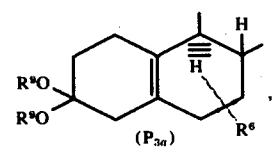
(P₃ₐ)
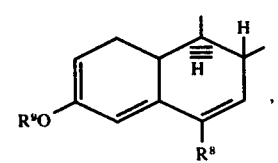
(P5a)
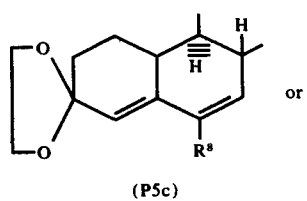
(P5c)
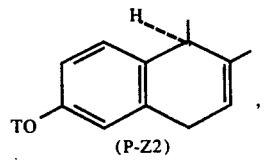
(P-Z2)
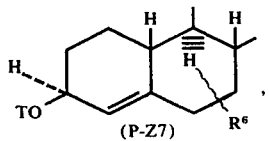
(P-Z7)
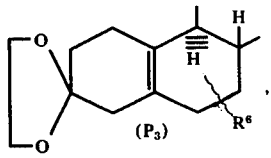
(P₃)
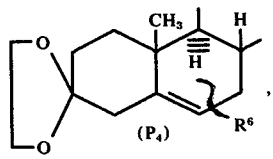
(P₄)
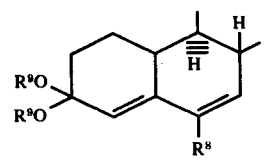
(P5b)
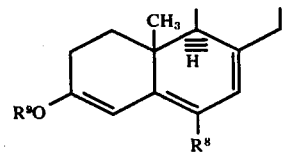
(P₅)
in which
T is tetrahydropyran-2-yl or tetrahydrofuran-2-yl;
R⁶ is a hydrogen atom, 6α-methyl or 7α-methyl;
R⁸ is a hydrogen atom, halogen having an atomic weight of from about 19 to 36, or methyl; and
R⁹ is alkyl having from 1 to 4 carbons and is linear.
58. The compound of claim 57 which is 3-methoxy-17α-propadienylestra-2,5(10)-dien-17β-ol.
* * * * *